United States Patent
Decker et al.

(10) Patent No.: US 7,413,551 B2
(45) Date of Patent: Aug. 19, 2008

(54) COMBINATION SELF ADJUSTING ENDOCERVICAL / EXOCERVICAL SAMPLING DEVICE AND CELL TRANSPORT / PRESERVATION SYSTEM

(76) Inventors: David Decker, 15 Mitchell Pl., Glen Ridge, NJ (US) 07028; Thomas DeAngelis, 7 Thomas Jefferson, Warren, NJ (US) 07059

( * ) Notice: Subject to any disclaimer, the term of this patent is extended or adjusted under 35 U.S.C. 154(b) by 0 days.

(21) Appl. No.: 11/162,890

(22) Filed: Sep. 27, 2005

(65) Prior Publication Data

US 2007/0073186 A1    Mar. 29, 2007

(51) Int. Cl.
*A61B 10/00* (2006.01)
(52) U.S. Cl. .................................... 600/569
(58) Field of Classification Search ............... 600/569, 600/570, 572; 604/1
See application file for complete search history.

(56) References Cited

U.S. PATENT DOCUMENTS

| | | | |
|---|---|---|---|
| 2,835,246 A | 5/1958 | Boettger | |
| 4,700,713 A | 10/1987 | Kist | |
| 4,754,764 A | 7/1988 | Bayne | |
| 5,022,408 A | 6/1991 | Mohajer | |
| 5,191,899 A | 3/1993 | Strickland et al. | |
| 5,279,307 A | 1/1994 | Mohajer | |
| 5,370,128 A * | 12/1994 | Wainwright | 600/569 |
| 5,422,273 A | 6/1995 | Garrison et al. | |
| 5,462,063 A | 10/1995 | Kist et al. | |
| 6,346,087 B1 * | 2/2002 | Peltier | 600/569 |

* cited by examiner

*Primary Examiner*—Max Hindenburg
*Assistant Examiner*—Jonathan M Foreman

(57) ABSTRACT

The device consists of a shaft with a detachable brush head. The brush head is a new design incorporating the utility of an expandable self adjusting area that yields a complete sample of the endocervix and exocervix regardless of varying individual anatomy. The brush head has protrusions disposed at strategic positions with flat surface collection areas. A ledge with protrusions samples the exocervical area and a middle portion samples the endocervical area. The middle portion automatically elongates from approximately 2 cm to 5.5 cm as to adjust to individual anatomies as the brush head is inserted into the cervical canal. The brush head is matched to a special collection container that permits the brush head to be detached and deposited into the container without the handling of the brush/head area. The special conical insert within the container automatically orients brush head for passage through horizontal slot at bottom of insert without operator's need to manually align. In this fashion the sampled cellular material can be completely, safely, and securely transported for laboratory evaluation.

1 Claim, 5 Drawing Sheets

Figures 3, 4, 5, 6:
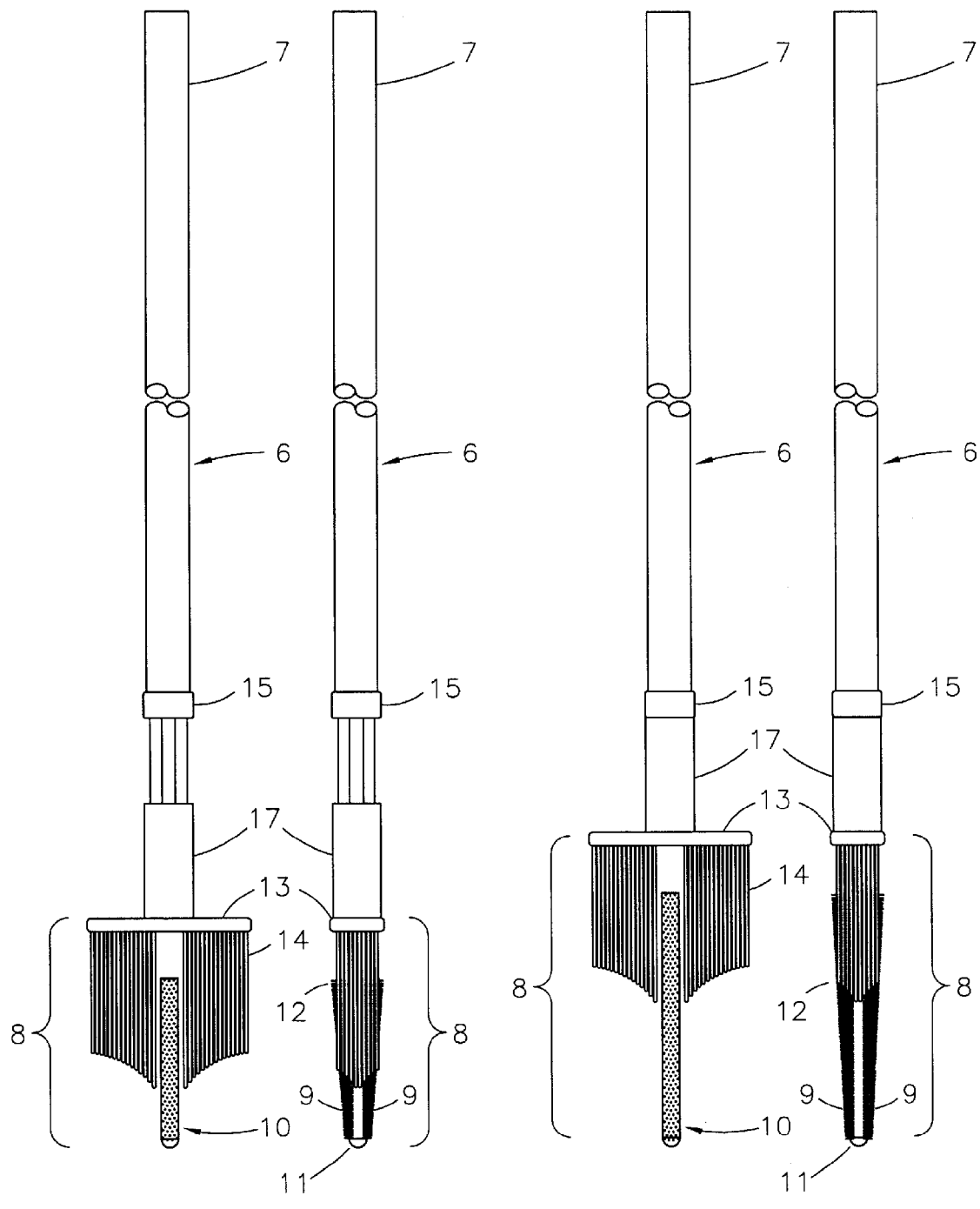

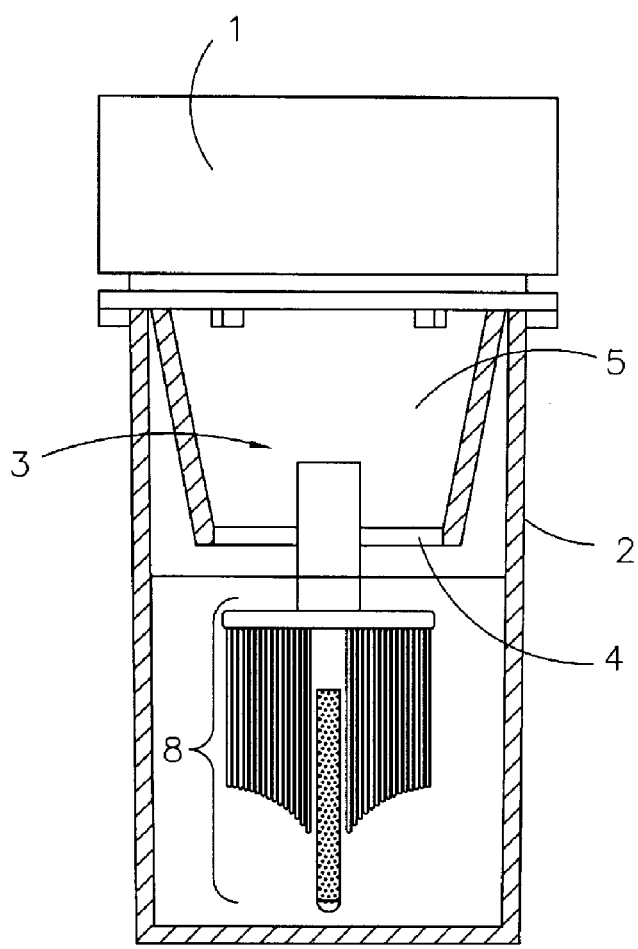
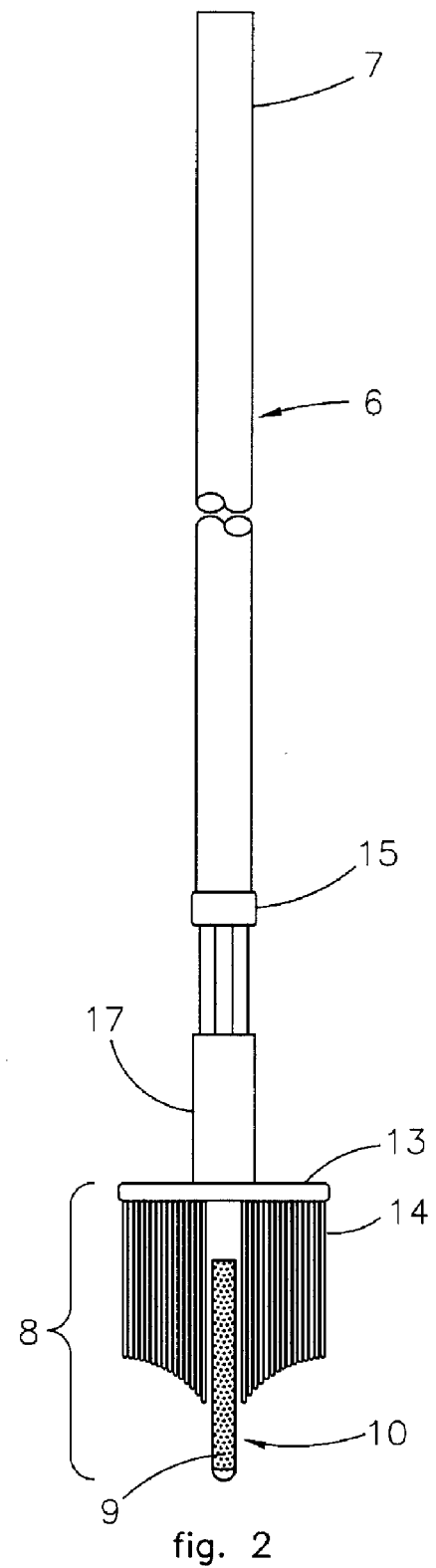
fig. 1
fig. 2

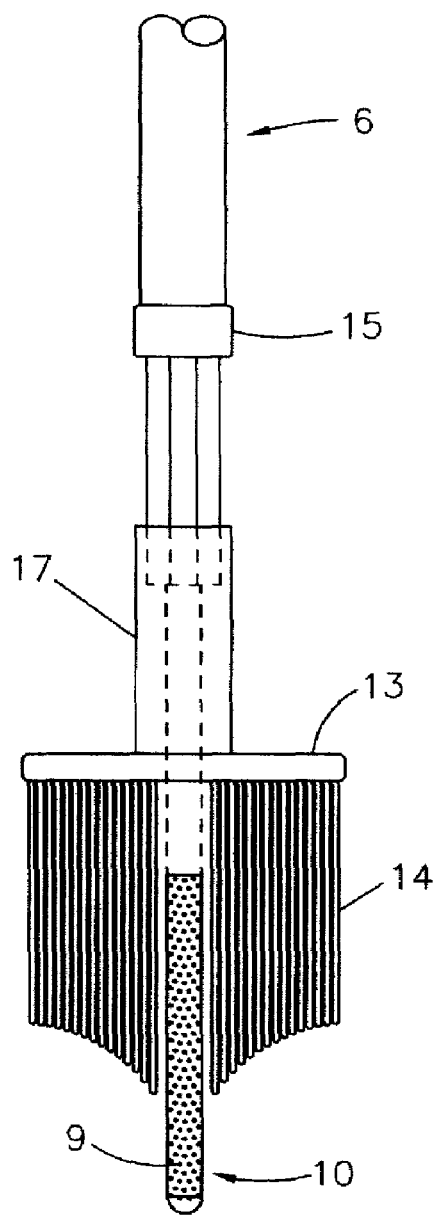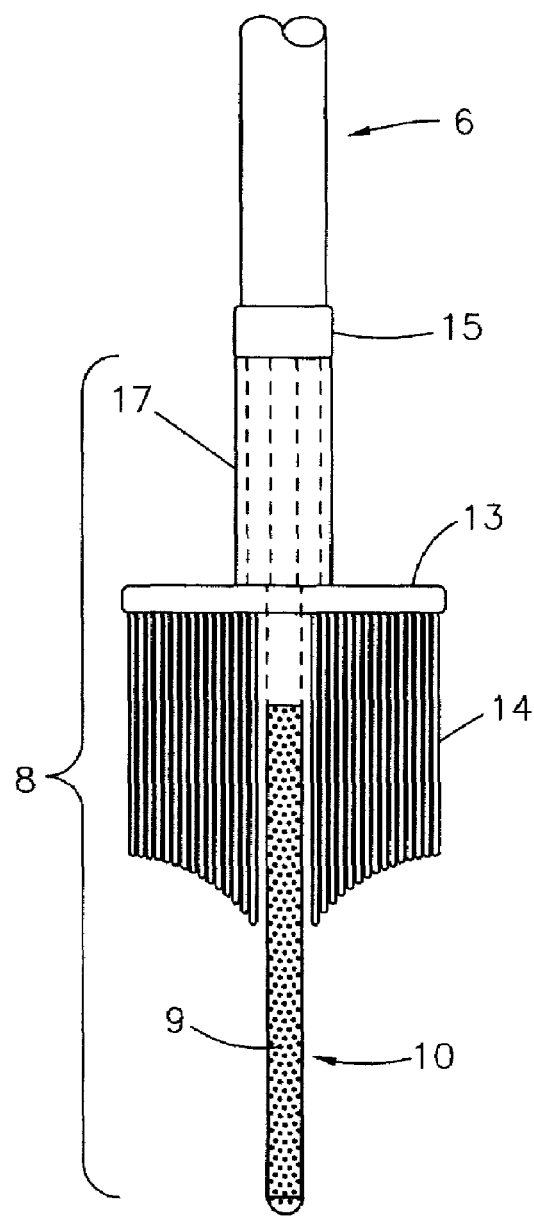
fig. 7
fig. 8

VIEW A—A

VIEW B—B

VIEW C—C

VIEW D—D

COMBINATION SELF ADJUSTING ENDOCERVICAL / EXOCERVICAL SAMPLING DEVICE AND CELL TRANSPORT / PRESERVATION SYSTEM

BACKGROUND OF THE INVENTION

This invention relates to the field of Cervical Cancer Screening with a new design and utility of both the sampling brush and transport system.

A pap smear is the most important screening tool to diagnose cervical cancer. The cervix has two cell types requiring sample, one each in the endocervical canal and the exocervix. Both of these cell types need to be seen by the pathologist with each and every pap screening sample. Cancers of the cervix develop both in the exocervical area and endocervical canal. Unfortunately the endocervical canal cannot be seen by the physician or healthcare provider. Due to this fact cancer of the cervix can be missed if the entire length of the endocervical canal is not sampled.

Currently there is no device available to the healthcare provider that automatically adjusts to the individual endocervical length and guarantee complete sampling. Currently the only way for the healthcare provider to guarantee sampling is with a two step process using two separate instruments.

Older combination brush designs that sample both the endocervical and exocervical cells have no methods employed that guarantee a complete sampling of the entire cervical canal. An example of this is the patient with a long endocervical canal which prevents the physician from discerning if the top of the cervix has been reached.

This brush design is self adjusting to the complete length of the endocervical canal.

Older brush and container designs require the brush to be washed in a solution within the container for cell collection. The brush, with still valuable cells, is then thrown away. Alternatively other current systems require the physical removal by handling and/or snapping off the brush or device tip. This has a drawback in that a loss and disruption of cellular material by human manipulation occurs when attempting to remove the brush head from the shaft. Other containers have a slot but the operator must look to facilitate alignment of the brush head with the slot.

With this more versatile design, the top of the brush can remain with the container after its removal from the shaft. All of the drawbacks of the earlier designs are eliminated with this new transport system. Operator's hands need not touch the brush head, preservative or sampled material. Not one collected cell is lost. Safely and cleanly removing the brush head from the shaft without contamination to the healthcare providers is also achieved with this system. There is no exposure to the mucous, blood, and cells of the cervix. The improved ease of operation is guaranteed due to the unique conical insert's ability to orient the brush head automatically without having to manually align.

SUMMARY OF THE INVENTION

This invention incorporates a new design in cervical sampling brushes. It also incorporates a transport system that eliminates the risk of losing cells due to contamination or poor operator manipulation of the brush head. It offers extreme ease of use and guarantee 100% collected cell retention and preservation.

Herein is the Exocervical/Endocervical Combination Brush. A unique design with utility to adjust for the varying endocervical canal length. As with other brush designs, there is a shaft (stem) which is ergonomically designed for easy maneuverability by the healthcare provider. The stem has an approximate length of 15-18 cm. At the opposite end is attached a removable head that incorporates the newly designed adjustable center section.

The removable head is where this design is completely different than any previous sampling brush. It is similar in that it has protrusions to sample the cells of the cervix. The difference is in the design of the shaft and it's attachment to the brush head at the most distal portion, not the most proximal as in all other brush head designs. Also, the center portion of the removable head is manufactured with a flexible, bellows, spiral cut, or similar process, so as the shaft advances into the endocervical canal, the flexible area begins to adjust to the length of the cervical canal going from approximately 2-5.5 cm as needed. As the process of opening, elongating, or stretching continues it should be noted that the exocervical portion of the brush has already contacted the outer cervix and is now ready to sample the face of the cervix. The combination brush is designed to accommodate varying endocervical lengths thus still being able to sample the complete cervix. Once the brush has been deployed to the proper position as determined by the cervical canal length, a sample is taken by rotation of the brush 360 degrees. It shall be noted that the endocervical protrusions are offset 90 degrees relevant to the exocervical protrusions as to ensure that they do not interfere with sampling of the endocervical canal. This design addresses all previous problems with similar yet less utilitarian brush designs for cancer screening and has the added benefit of requiring a single step for accurate and complete samples of both the endocervical and exocervical cellular material.

The second part of the new design is the containment system. This container facilitates the collection, preservation, and transportation of the sample. The new design of the vessel provides for an easy single step removal of the brush head without operator contamination and yields the best possible cell collection. The vessel is designed with a cone shaped molded insert witch includes an opening at its base which allows the brush head to orient itself automatically into opening. The operator does not need to align the brush head with the opening due to the conical shape of the insert. Once through the slot the operator, holding the stem, simply rotates the brush in either direction and gently lifts upward while holding the vessel. The head falls off into the preservative. The vessel is then closed normally. The container can then be gently shaken to facilitate cell separation from brush head.

This container removes the risk of splattering cellular debris. Also eliminated is the risk of contaminating the brush head on removal as is now possible with older brush designs. Further advantage is the elimination of risking valuable cell loss as the operator manipulates old brush styles during stirring and/or head removal. All this with ease of use due to the unique tapered conical insert. Therefore, there is a reality of preserving 100% of the collected cellular materials for transport.

BRIEF DESCRIPTION OF THE DRAWINGS OF THE PREFERRED EMBODIMENTS

FIG. 1 of sheet 1 is a cross section view of the containment, preservation, and transport vessel. Brush head is free from stem and sealed in container for transportation.

FIG. 2 of sheet 1 is a plan view of the 2 piece combination exocervical/endocervical sampling brush. Brush is in its assembled and fully retracted (relaxed) position.

FIG. 3 of sheet 2 is identical to FIG. 2 and has been included on sheet 2 for clarification and consistency when viewed aside FIG. 4, FIG. 5, and FIG. 6 on sheet 2. The purpose is to illustrate the brush in its retracted (relaxed) position.

FIG. 4 of sheet 2 is FIG. 3 rotated 90 degrees to illustrate side plan view.

FIG. 5 of sheet 2 is a plan view of the 2 piece combination exocervical/endocervical sampling brush. Brush is in its assembled and fully extended (elongated) position.

FIG. 6 of sheet 2 is FIG. 5 rotated 90 degrees to illustrate side plan view.

FIG. 7 of sheet 3 illustrates close-up embodiment of the brush head in the fully retracted state. Also demonstrated via the hidden lines are the details of the internal utility of the stem and socket design.

FIG. 8 of sheet 3 illustrates close-up embodiment of the brush head in the fully extended state. Also demonstrated via the hidden lines are the details of the internal utility of the stem and socket design.

Figure 9:
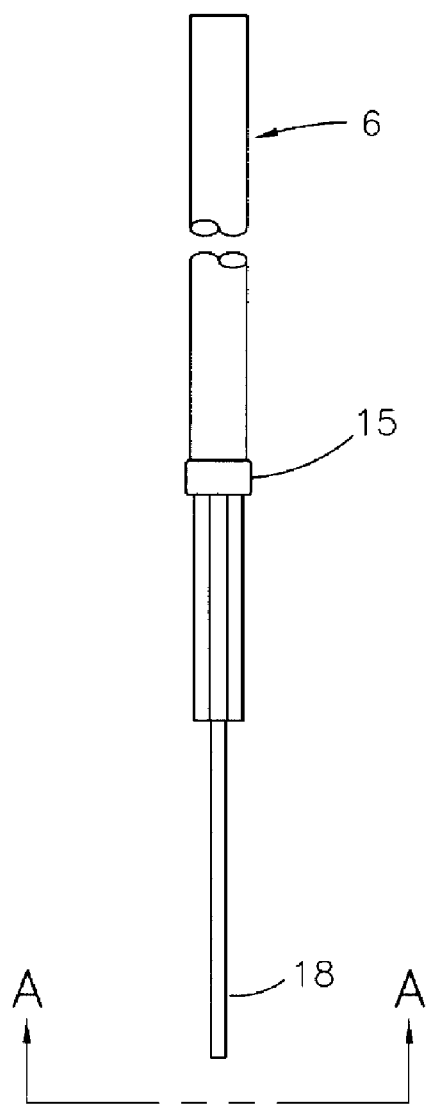
Figure 9:
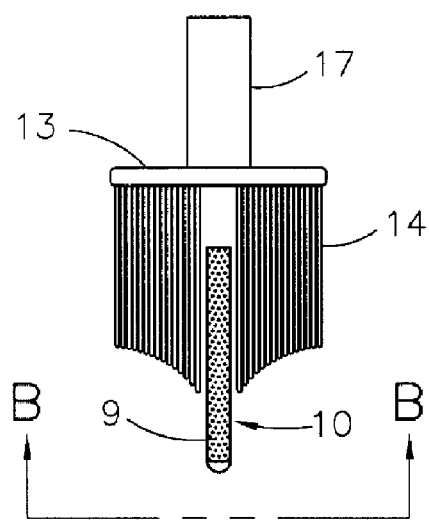

FIG. 9 of sheet 4 is an exploded view showing the embodiment and means of assembly of the brush and stem.

Figure 10:
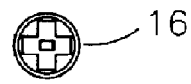

FIG. 10 of sheet 4 is a view (A-A) detailing keyed stem design.

Figure 11:
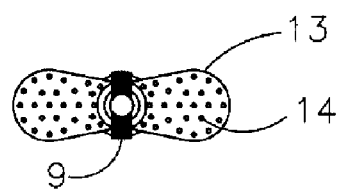

FIG. 11 of sheet 4 is a view (B-B) detailing brush shelf, exocervical protrusions, and endocervical protrusions as well as their relative positions to each other.

Figure 12:
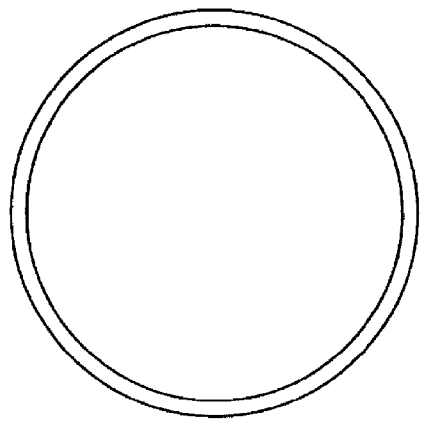

FIG. 12 of sheet 5 is the top view (C-C) of the sealed containment vessel.

Figure 13:
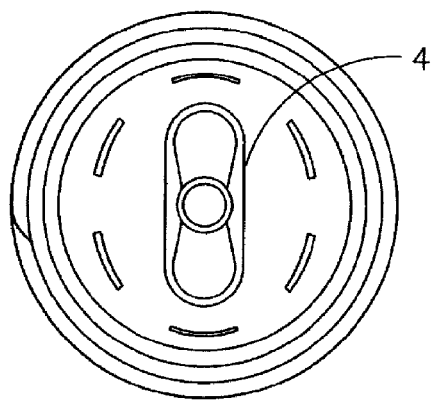

FIG. 13 of sheet 5 is the top view (D-D), rotated 90 degrees when compared to FIG. 12, of the open containment, preservation, and transport vessel.

Figure 14:
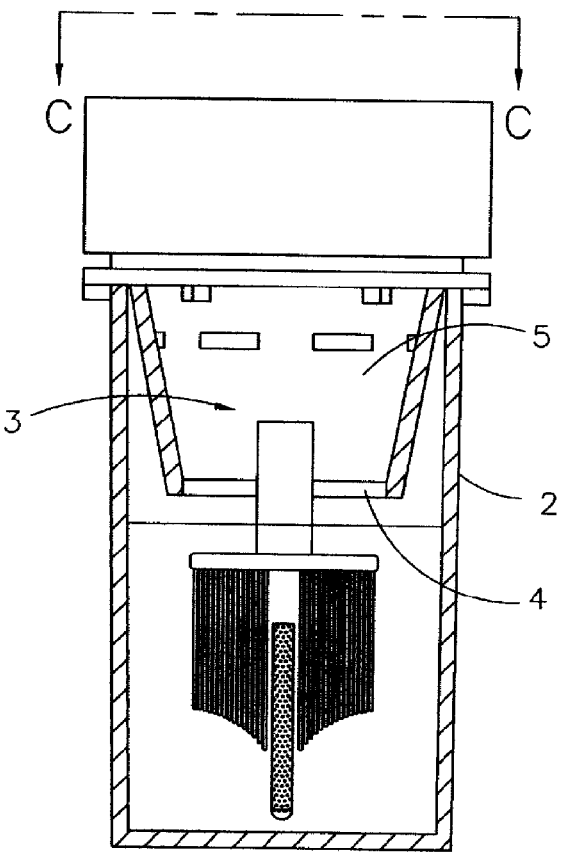

FIG. 14 of sheet 5 is a cross section view of the closed containment, preservation, and transport vessel. Brush head is free from stem and sealed in container for transportation.

Figure 15:
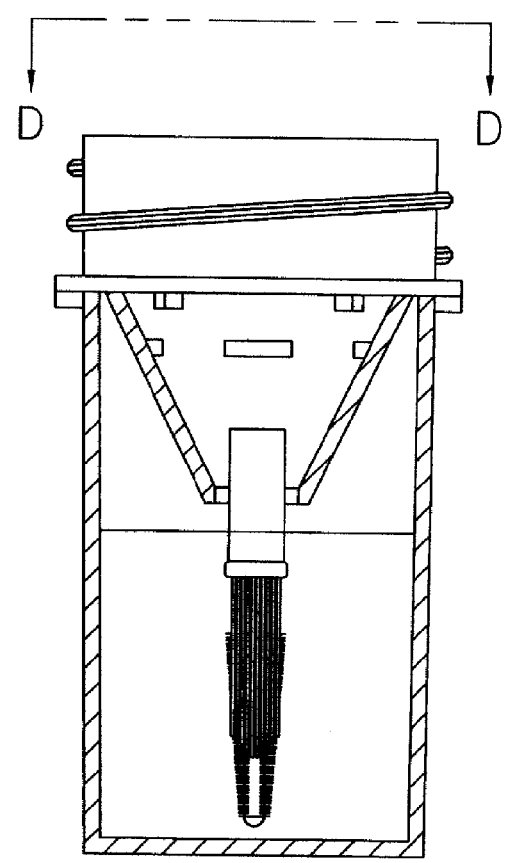

FIG. 15 of sheet 5 is a cross section view, rotated 90 degrees when compared to FIG. 14, of the open containment, preservation, and transport vessel. Brush head is free from stem and oriented in container.

DETAILED DESCRIPTION OF THE PREFERRED EMBODIMENTS

Cervical Brush

A Combination Self Adjusting Endocervical/Exocervical Cellular Sampling Device.

Referring to the drawings:

In FIG. 2 is shown a combination self adjusting cervical sampling device constructed according to said invention.

In FIGS. 3-6 illustrates the cervical sampler comprising an elongated handle (6) having a free end (7) and a removable head (8).

FIG. 8 shows the removable head section in its elongated position. Rows of flexible endocervical protrusions (9) are disposed on the center section (10) of head (8). As seen in FIGS. 4 and 6, each of the protrusions (9) is configured to have two opposing surfaces. The protrusions are flexible as to cause the least amount of deep penetration of the endocervical tissue. Cells are collected on the flat surfaces of the protrusions (9) regardless of rotation of brush. Protrusions (9) are disposed on center section (10) directly opposed 180 degrees from each other. The Protrusions are perpendicular to the center section (10). Protrusions (9) are tapered in length such that the most distal protrusions (11) have the shorter length and the most proximal the longest (12).

Protrusions (9) are integrated into removable head (8) and are part of the expandable and self adjusting center (10). The removable head (8) has a shelf member (13) which is wider, flexible and stronger to support the protrusions (14) for the exocervix. It also acts as a stop for advancement of the removable head onto the cervical "os" allowing the center section to continue advancing to the full depth of the endocervical canal demonstrating its self adjusting utility.

Exocervical protrusions (14) are parallel to adjustable section (10). Protrusions (14) are constructed to have the longest length near the center section (10) and shortest length at the ends of the shelf member (13).

Protrusions (14) have square or rectangular shape so a firm edge is available to wipe cellular material from exocervix. Rotation of device can be in clockwise or counter clock wise direction.

The device is introduced into the vagina and then disposed onto the mouth of the cervix; protrusions (14) spread out as the device is advanced. The center adjustable section continues to enter the endocervical canal. As the device continues to advance, and resistance to advancement increases at the exocervix, the center section with less resistance continues to advance in the endocervical canal to its full extent. Cervical sample is taken by a 360 degree gentle rotation. Full elongation of the center section (10) is easily perceived by the resistance of the closed internal "os".

FIG. 9-10 shows new and unique socket and shaft matching male and female components. Shaft (6) has stop collar (15) with noted crisscross guide (16) matched to hub (17) of removable head (8). This prevents slippage of removable head about the axis of rotation. Further distal final section of shaft (18) fits into above said socket notch at the tip of expandable section of removable head (8). Taper fit with most distal portion of expandable section (10) locks shaft (18) in place.

This invention is not restricted to embodiment shown in the drawing by way of example which can be varied in many different ways. It may be constructed with different shapes and number of protrusions, removable head may also have different shape in relation to flag placement.

Collection Device

The second component is a collection device that complements the combination cervical brush's removable head. A specially designed vessel is seen to receive, preserve, and transport the brush head.

Referring to the drawings:

FIG. 1 shows threaded lid (1) with seal on container (2). Vessel is constructed with a unique insert (3). It is constructed such that a horizontal opening (4) with conical side wall (5) is formed and continually narrows to the horizontal opening.

FIG. 13 depicts horizontal opening (4) which is just large enough to easily admit removable head through opening. Enough depth is available to admit head completely below the opening. At this time a 90 degree rotation of the head and shaft orient the removable head into a position that cannot fit through the horizontal opening (4). It is at this time that the operator, now holding the vessel, pulls shaft upward allowing the removable head to easily drop from the shaft. The lid is then screwed on for proper seal and eventual transport to laboratory facilities.

What is claimed is:

1. A system for the collection and transport of endocervical and exocervical cells comprising:
   a brush including a removable head portion and a shaft portion;
   the removable head portion including a hub portion, a shelf member and an expandable section; the expandable section being aligned with the center of the shelf member and the hub portion; the expandable section having flags disposed perpendicular thereon for collection of endocervical cells, the flags being shorter in length at the distal portion of the expandable section and longer at a most proximal portion of the expandable section, the shelf member including flags thereon parallel to the expandable section for the collection of exocervical cells, the flags being longer nearest the expandable section and shortest at ends of the shelf member;

said shaft portion including a stop collar proximal a crisscross guide matched to a socket within said hub portion; said shaft portion including a final section distal the crisscross guide adapted to lock into a tapered section of the distal portion of said expandable section;

wherein upon introduction into the vagina, said shelf member abuts the outer cervical surface to stop the advancement of said removable head, whereby the expandable section continues to advance into the endocervical canal; and a container including a removable lid, a preservative, and a cone shaped insert including an opening adapted to receive said removable head portion; wherein rotating the brush approximately ninety degrees and lifting said shaft portion upon entry of said removable head portion past said opening allows separation of the removable head portion from said shaft portion.

* * * * *